(12) United States Patent
Baumann et al.

(10) Patent No.: US 8,718,765 B2
(45) Date of Patent: May 6, 2014

(54) DEVICE FOR ADAPTIVE PROCESSING OF AN ENDOCARDIAL ACCELERATION SIGNAL

(75) Inventors: Oliver Baumann, Southampton (GB); Lionel Giorgis, Saint Brieuc (FR)

(73) Assignee: Sorin CRM SAS, Clamart Cedex (FR)

( * ) Notice: Subject to any disclaimer, the term of this patent is extended or adjusted under 35 U.S.C. 154(b) by 0 days.

(21) Appl. No.: 13/423,881

(22) Filed: Mar. 19, 2012

(65) Prior Publication Data

US 2012/0245853 A1  Sep. 27, 2012

(30) Foreign Application Priority Data

Mar. 18, 2011 (FR) ...................................... 11 52271

(51) Int. Cl.
  *A61N 1/365* (2006.01)
(52) U.S. Cl.
  USPC .......................................................... 607/17
(58) Field of Classification Search
  USPC .................. 607/17, 18, 23–25; 600/527, 528
  See application file for complete search history.

(56) References Cited

U.S. PATENT DOCUMENTS

| | | | |
|---|---|---|---|
| 5,255,186 A | 10/1993 | Steinhaus et al. | |
| 5,304,208 A | 4/1994 | Inguaggiato et al. | |
| 6,280,394 B1 | 8/2001 | Maloney et al. | |
| 2005/0131470 A1 | 6/2005 | Vitali et al. | |
| 2009/0209875 A1* | 8/2009 | Giorgis et al. | 600/512 |

FOREIGN PATENT DOCUMENTS

| | | |
|---|---|---|
| EP | 0515319 A2 | 11/1992 |
| EP | 1533001 A1 | 5/2005 |
| EP | 2092885 A1 | 8/2009 |

OTHER PUBLICATIONS

FR, Foreign Search Report (Annexe Au Rapport De Recherche Preliminaire Relatif A La Demande De Brevet Francais No. FR 1152271 FA 748951), Oct. 24, 2011.

* cited by examiner

*Primary Examiner* — George Evanisko
(74) *Attorney, Agent, or Firm* — Foley & Lardner LLP

(57) ABSTRACT

Device for adaptive processing of an endocardial acceleration signal. The device continuously collects an endocardial acceleration EA signal and divides it into EA sub-signals, each over the duration of one cardiac cycle. The EA sub-signals are separated into the EA1 and EA2 components. A cross-correlation between the EA sub-signals of each component and a time calibration compared to a reference cycle, and a series of validation criteria is applied. The result is an average overall EA signal for a cycle. A change in the patients condition or an occurrence of a predetermined event in the patient is detected (24) and, as a result there is dynamic adaptation of at least one of said validation criteria and/or at least one of the pre-processing parameters for calculating the EA signal average.

4 Claims, 3 Drawing Sheets

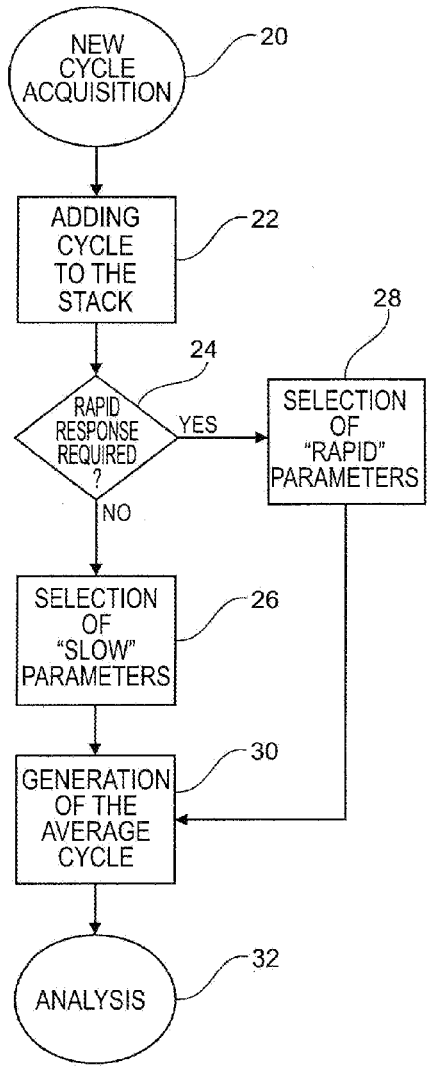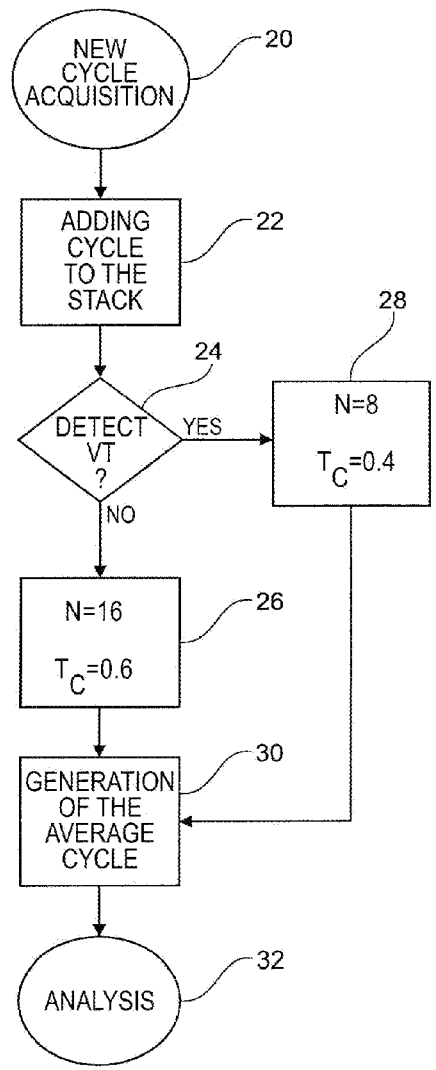
FIG. 7                    FIG. 8

DEVICE FOR ADAPTIVE PROCESSING OF AN ENDOCARDIAL ACCELERATION SIGNAL

FIELD

The present application claims the benefit of French Application No. 11/52271 entitled "Device For Adaptive Processing Of An Endocardial Acceleration Signal" and filed Mar. 18, 2011, which is hereby incorporated by reference in its entirety.

The present invention relates to "active implantable medical devices" as defined by the 20 Jun. 1990 Directive 90/385/EEC of the Council of the European Communities, more particularly to devices that continuously monitor a patient's heart rhythm and deliver to the heart, if necessary, electrical pulses of stimulation, defibrillation and/or resynchronization, in case of a disorder detected by the device. The present invention even more particularly relates to such devices that are provided with an endocardial acceleration sensor.

BACKGROUND

Active implantable medical devices are known that include an endocardial acceleration sensor (an "EA sensor"). The signal delivered by an EA sensor (hereinafter "EA signal") is processed and analyzed by various algorithms for, among other things, diagnosis, control of the device, and search for pacing configurations providing the best hemodynamic efficiency.

Several clinical studies have shown that endocardial acceleration is a parameter that accurately and in real-time reflects the phenomena related to the contractions and relaxations of the heart muscle, and can therefore provide comprehensive information on the cardiac mechanics in the case of normal operation as well as in the case of a deficient operation.

The EA signal can be decomposed into two components corresponding to the two successive major heart sounds (S1 and S2 sounds of the phonocardiogram): the EA1 component, which begins following the QRS complex, is caused by a combination of closing the atrioventricular valves, opening the semilunar valves, and the contraction of the left ventricle; the EA2 component, which follows, is associated with the end of the ventricular systole and is generated by the closure of the semilunar valves. The EA signal may contain one or two other distinguishable components, called EA3 and EA4, respectively corresponding to the S3 and S4 sounds of the phonocardiogram.

EP 2092885 A1 and its counterpart US Patent Publication No. 2009/0209875 (both assigned to Sorin CRM S.A.S., previously known as ELA Medical) describes a device implementing an improved technique for EA signal analysis which allows extraction of some meaningful information, representative of the hemodynamic and mechanical activity of the patient's heart. This technique operates a signal averaging and a realignment of its components over several successive cycles. This effectively eliminates the influence of cycle to cycle variations of the EA signal which may distort the results delivered by the algorithm analyzing the EA signal.

Specifically, this technique performs a pre-processing of the continuously collected EA signal, which:

Divides the EA signal into sub-signals, each sub-signal corresponding to the duration of one cardiac cycle and being identified by a cycle start marker representing the separation of cycles;

Segments each of the sub-signals in order to individualize the EA1 and EA2 components in a given time window;

For the current EA1 (or EA2) component thus isolated on a given cycle, searches for a cross-correlation peak with respect to the EA1 (or EA2) components collected from other cycles;

Calculates a corresponding time calibration;

Applies the calculated time calibration to the current component, so as to align it with respect to the other components, and Averages the various sub-signals as realigned in order to produce an average EA signal for a cycle, with elimination of the bias of the cycle to cycle variability.

The EA signal averaging over several cycles reduces the influence of cycle to cycle variations of the signal, but it introduces a time constant that becomes larger as the average is calculated over a larger number of cycles.

The choice of the preprocessing parameters of the EA signal is therefore based on a compromise between accuracy (which increases as the averaging is performed over a larger number of cycles) and fast response.

Thus, a calculation based on a relatively small number of cycles, typically five cycles as described in the aforementioned document, provides a near real-time monitoring of the evolution of the EA signal, but at the cost of some noise contamination due to the instability of the EA signal, and thus less reflects the mechanical and hemodynamic activity of the patient's heart. Similarly, the criteria for acceptance or rejection of data for a given cycle in the average calculation is more or less rigorous depending on whether the reference cycle is calculated based on a large number of elementary cardiac cycles, with consequently a higher or lower risk of introducing atypical cycles (such as extrasystoles) in the computation of the average.

OBJECT AND SUMMARY

It is, therefore, an object of the present invention to provide an improved signal processing of the EA signal overcoming the aforementioned compromise, by use of a dynamic adaptation of the conditions for calculating the average signal.

One aspect of the present invention is directed to a device comprising, as disclosed in EP 2092885 A1 and its counterpart US Patent Publication No. 2009/0209875: means for continuously collecting an EA signal over a sequence of N cardiac cycles; means for dividing the collected EA signal over EA sub-signals, each corresponding to the duration of one cardiac cycle; means for isolating in each of the EA sub-signals, for the length of a respective analysis window, at least one EAx component associated with the one of the heart sounds Sx, where Sx is S1, S2, S3 or S4 for this sub-signal; means for operating a cross-correlation between the EA sub-signals of said at least one EAx component, for defining a reference cycle, for determining for each cycle a correlation coefficient and a time calibration of the EAx component compared to the reference cycle, and for operating a time calibration of the EAx component relative to the reference cycle; means for applying to the EA sub-signals and to the EAx components associated with the sequence of N cardiac cycles a series of validation criteria and retaining only the N' cycles that meet these criteria, where N'≤N; and means for averaging the N' cardiac cycles, and delivering an average overall output EA signal over a cycle.

According to one embodiment of the present invention, the device further comprises means for detecting a change in the patient's condition or an occurrence of a predetermined event in the patient, and means for dynamically adapting, on detection of said change of state or said predetermined event, at least one of said validation criteria and/or at least one of the pre-processing parameters. The means for dynamically adapting are more preferably means for modifying of at least one of the following preprocessing parameters: a number N of cycles of the sequence to be collected and processed, an interval or step between two successive collected and processed sequences, and a duration of said analysis window of the EAx component.

In another embodiment, the means for dynamically adapting is a means for modifying at least one of the following validation criteria: a minimum threshold for the coefficient of correlation with respect to the reference cycle, a maximum threshold for said temporal calibration compared to the reference cycle; a minimum number of cycles for the N' cycles selected by the selection means; and, in an embodiment employing multiple EAx components isolated in each EA sub-signals, selection of the only EA sub-signals for which all the associated EAx components meet the validation criteria.

In one embodiment, the change of state or predetermined event may be selected from the group consisting of: an increased heart rate, a determined heart rate instability, a decreased amplitude of the peak of endocardial acceleration, an increased breathing rate, a detection of an apnea condition, and an application of an external command.

Although the present application is generally described in the context of an EA signal, it should be understood that other signals indicative of the patient's cardiac activity may be used such as a cardiac electrogram (EGM) or other pressure signal.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which:

FIG. 7 is a schematic flow chart of a first embodiment of an algorithm for selection of the parameters according to the invention; and FIG. 8 is a schematic flow chart of a second embodiment, homologous to FIG. 7, for a practical example of adjustment of the processing parameters based on the detection or absence of ventricular tachycardia (VT).

DETAILED DESCRIPTION

With reference to the drawings FIGS. 1-8, a preferred embodiment of a device according to the present invention will now be described.

As for the software aspect, the present invention may be implemented by appropriate programming of the control software that exists in an active implantable medical device, e.g., a pacemaker, a resynchronizer and/or a defibrillator, that acquires a signal that is collected by endocardial leads and/or one or more implanted sensors. The present invention may particularly be applied to implantable devices such as those of the Paradym and Ovatio device families produced and marketed by Sorin CRM, Clamart France, formerly known as ELA Medical, Montrouge, France.

These devices include programmable microprocessor circuitry to receive, format, and process electrical signals collected (detected) by electrodes implanted in a patient, and deliver electrical pulses to these electrodes, e.g., for stimulation. It is possible to transmit by telemetry software instructions that will be stored in a memory of the implantable devices and executed to implement the functions of the present invention that will be described herein. The adaptation of these devices to implement the functions and features of the present invention is believed to be within the abilities of a person of ordinary skill in the art, and therefore will not be described in detail.

Figure 1:
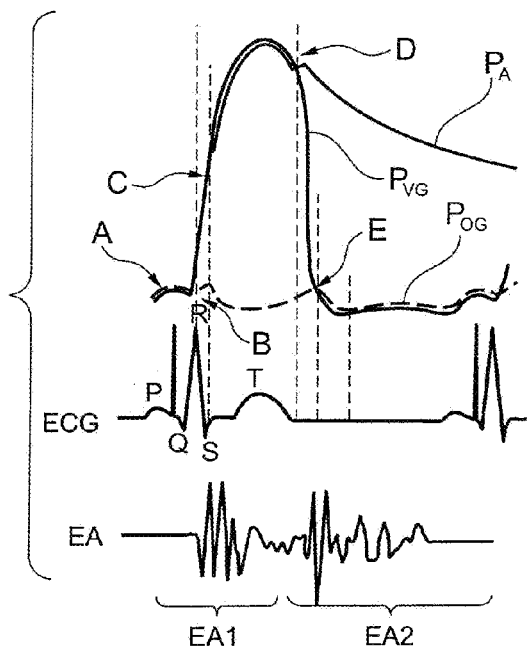
FIG. 1 is a series of three timing diagrams illustrating various signals characterizing the cardiac activity during a given cardiac cycle.

With reference to FIG. 1, the different well-known signals characterizing the activity of a patient's heart during a cardiac cycle, are shown, including: the profile of intracardiac pressures ($P_A$, $P_{VG}$ and $P_{OG}$), a record of a surface electrocardiogram (ECG), and the variations of the endocardial acceleration signal (EA). The $P_A$ characteristic represents the variations in aortic pressure, $P_{VG}$ represents the variations in the left ventricular pressure and $P_{OG}$ represents the pressure variations in the left atrium. Points A to E correspond to the different mechanical phases: A contraction of the left atrium, B closure of the mitral valve, C opening of the aortic valve, D closure of the aortic valve, E opening of the mitral valve. The ECG signal has successively the P wave corresponding to the depolarization of the atria, the QRS complex corresponding to the depolarization of the ventricles and the T wave of ventricular repolarization. The endocardial acceleration ("EA") can be measured by an accelerometer in direct contact with the heart muscle (usually at the right ventricular apex, sometimes in the right atrium, or against the septum), which produces an EA signal corresponding to the EA of the patient's heart.

EP0515319A1 and its counterpart U.S. Pat. No. 5,304,208 (both assigned to Sorin Biomedica Cardio SpA) teach one useful method and apparatus to collect an endocardial acceleration signal using an endocardial lead equipped with a distal stimulation electrode located at the apex of the ventricle and integrating a microaccelerometer for measuring the endocardial acceleration, which is incorporated herein by reference in its entirety.

The EA signal collected during a cardiac cycle forms two main components, corresponding to the two major heart sounds (namely the S1 and S2 sounds of the phonocardiogram) it is possible to recognize in each cardiac cycle:

The first component of endocardial acceleration ("EA1"), whose amplitude variations are closely linked to the variations in pressure in the ventricle (the maximum peak-to-peak amplitude of this component EA1, called PEA1, is specifically correlated with the positive maximum of the pressure variation dP/dt in the left ventricle) and thus can provide a parameter representative of the myocardial contractility, which is itself linked to the level of activity of the sympathetic system;

The second component of endocardial acceleration ("EA2") which occurs during the phase of isovolumetric ventricular relaxation. This second component is mainly produced by the closure of the aortic and pulmonary valves.

The EA signal may contain one or two other components, called EA3 and EA4 and corresponding to the S3 and S4 sounds of the phonocardiogram and which the more often indicate heart failure (EA3 being related to vibrations of the walls of the myocardium during rapid filling, and EA4 being related to the atrial contraction).

The term "EAx component" as used herein refers hereafter to one of these four components, more preferably to designate either the EA1 or the EA2 component.

Given the relatively large cycle to cycle variability of the EA signal, the analysis of the EA signal usually involves conducting an averaging over several cycles in order to have an average overall EA signal, defined over the duration of one cycle, which is representative of the hemodynamic activity of the patient's heart and can then be applied to various algorithms for analysis, diagnosis, etc.

Figure 2:
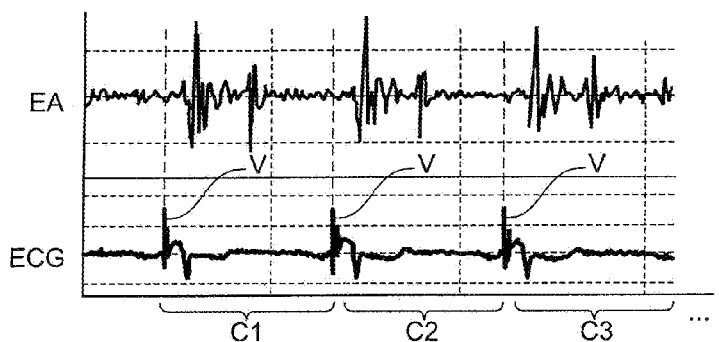
FIG. 2 illustrates a representative breakdown of a continuous recording of an
EA signal and an electrocardiogram (ECG) signal for a series of successive cardiac cycles.

As noted, the present invention is directed to the pre-processing step which concerns averaging the EA signal over several EA cycles. The EA signal being continuously collected, it is first necessary to segregate the collected EA signal into information corresponding to the successive cardiac cycles. For this purpose, as shown in FIG. 2, the successive cardiac cycles C1, C2, C3 ... CN of the continuous EA signal is defined by markers representing the beginning of the cycle and segregate the cardiac cycles, to produce a series of EA sub-signals, each corresponding to a period of one cardiac cycle. These markers of the beginning of a cardiac cycle can be provided by, for example, the device itself, which conventionally already stores either the V pacing instants (as shown in FIG. 2) or the R-wave detection instants, according to the mode of operation, a stimulation peak detection algorithm, or detection of the QRS complexes of the ECG signal.

This step can also optionally implement a known algorithm for detection of extrasystoles to eliminate from the calculation those cardiac cycles affected by detected extrasystoles. More preferably, the cycle preceding the extrasystole, the cycle including the extrasystole itself, and the cycle following the extrasystole (hereinafter referred to as "insignificant cycles") are identified and excluded from the calculations. The EA signal to be processed in this embodiment is the signal continuously collected by the EA sensor without the insignificant cycles.

Figure 3:
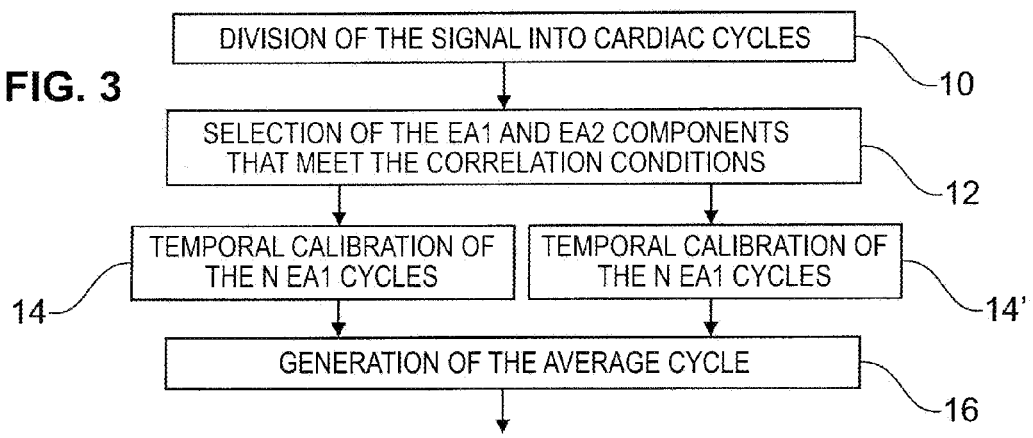
FIG. 3 is a schematic flowchart of a process for averaging the EA signal for later analysis.

The processing leading to the averaged EA signal will now be explained with reference to the flowchart in FIG. 3. The first step, referenced 10 in FIG. 3, is to segregate, as explained above, a number N of successive cardiac cycles by division of the EA signal continuously collected and preferably previously filtered by a bandpass filter. The next step is to designate a parameter "step" corresponding to the calibration step between two groups of N cycles, thus, corresponding to the generation of two successive average overall EA signals.

The EA signal analysis can be performed using a sliding analysis window (thus with an overlapping between two sets of N successive processed cycles) of N beats, typically N=5 to 20 cycles to follow the temporal evolution of the different characteristics of the EA signal with a follow-up step corresponding to the step parameter, e.g. step=5 cycles.

The individual cycles are then normalized by calculation of an average cycle length, or a median cycle length, of N successive beats, and re-adjustment on this common median length $RR_{med}$ of the individualized fractions of the EA signal, in order to obtain a signal with the same number of samples for each individual cycle.

After this adjustment, a matrix composed of N EA sub-signals is obtained, all having the same length (equal to the calculated $RR_{med}$ median).

The next step, corresponding to the block 12 of FIG. 3, is to isolate each EA sub-signal from both the EA1 and EA2 components, so as to then perform a number of processing steps separately for each of these EA1 and EA2 components.

The extraction of two EA1 and EA2 components is operated by a correlation technique applied to N EA sub-signals.

Figure 4:
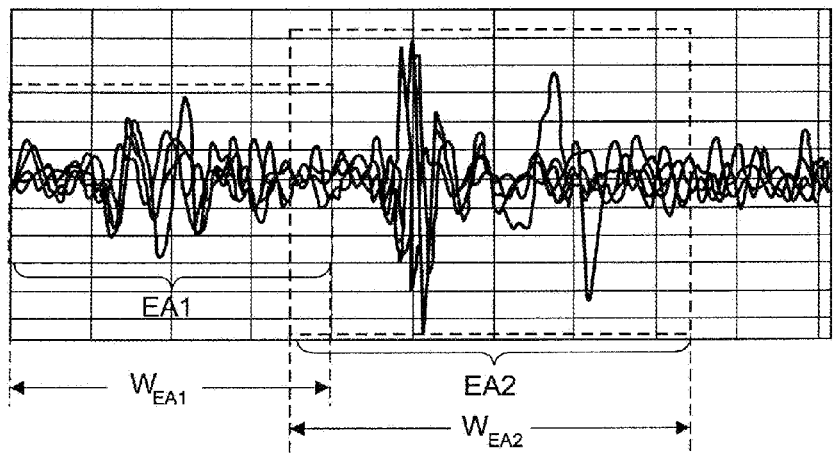
FIG. 4 illustrates a representative extraction of the EA1 and EA2 components for an EA sub-signal.

FIG. 4 shows the two windows of the useful EA1 and EA2 signal obtained by exploiting the reproducibility of the two EA1 and EA2 components on the N EA sub-signals. The duration of each of these windows is a configurable value $W_{EA1}$, $W_{EA2}$. Note that the two windows of the useful EA1 and EA2 signal may be partially overlapping.

From the matrix of the N EA sub-signals, two independent matrices containing the respective samples ea_cycles1 (t) and ea_cycles2 (t) of the EA1 and EA2 components of the N analyzed cardiac cycles is obtained.

The next step referenced 14 or 14' in FIG. 3, is to operate a temporal calibration of the N cycles, separately and in parallel for each of the two EA1 and EA2 components (the same processing being performed for each of the two components). The technique used is, for example, for each pair of sub-signals of the EA1 or EA2 matrix, to seek the maximum of the normalized cross-correlation function, a function that varies between 1 (in the case of two perfectly correlated vectors) and 0 (in the case of two uncorrelated vectors):

$$\Gamma_{i,j}(\tau) = \frac{\sum_{t=0}^{Nsamples-\tau-1}(ea\_cycles_i(t+\tau) - \mu_{ea\_cycles_i}) \cdot (ea\_cycles_j(t) - \mu_{ea\_cycles_j})}{\sqrt{\sum_{t=0}^{Nsamples-1}(ea\_cycles_i(t) - \mu_{ea\_cycles_i})^2 \cdot \sum_{t=0}^{Nsamples-1}(ea\_cycles_j(t) - \mu_{ea\_cycles_j})^2}}$$

Figure 5:
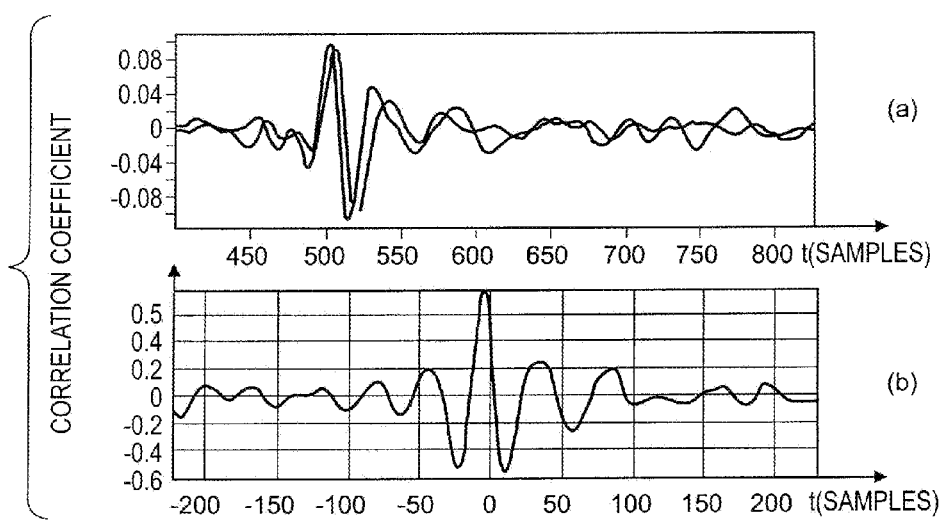
FIG. 5 illustrates an example of a calculation of cross-correlation functions between two EA sub-signals, to realign the components of the successive various cycles.

The result is shown in FIG. 5: FIG. 5a shows the pair of analyzed sub-signals and FIG. 5b the corresponding cross-correlation function. In the example in FIG. 5, the maximum of the cross-correlation function is at $\tau_{i,j}=-5$ samples, with a peak value of 0.78: this means that by delaying $ea\_cycles_1$ (t) of 5 samples, $ea\_cycles_1$ (t) and $ea\_cycles_2$ (t) are correlated with $\Gamma=0.78$.

Then two tables are constructed:

One containing correlation coefficients r the different pairs, and

One containing the delays $\tau_{i,j}$ to readjust or calibrate the different sub-signals $ea\_cycles_i(t)$ against each other.

Then the cycle that best correlated to other $ea\_cycles_i(t)$ (i≠J) is identified, by calculating for each i the average correlation coefficient with the other sub-signals. The sub-signal having the maximum average correlation coefficient is the reference sub-signal reference_cycle_ind_EAx. Among the sub-signals ea_cyclesj(t) (with j≠reference_cycle_ind_EA$_x$) thus obtained, only those that meet the following criteria are retained:

$r_{reference\_cycle\_ind\_EAx,j}$ > Correlation threshold_EA$_x$,
and $|\tau_{reference\_cycle\_ind\_EAx,j}|$ < Correlation threshold delay _EA$_x$, The two parameters Correlation threshold_EA$_x$ and Correlation threshold delay_EA$_x$ allow elimination in the subsequent calculation of the average a number of atypical cycles, which could distort the result and lead to "noisy" average values which are difficult to exploit.

Of the N original signals, $N'_{EAX} EA_X$ cycles remain after this selection step. At this point, it is checked if the number $N'_{EAx}$ of correct $EA_X$ cycles is at least equal to a minimum number $N'EA_{x\_}min$ of cycles for both components EA1 or EA2.

If this condition is not satisfied, that is to say if one of the two components EA1 or EA2 did not satisfy the condition $N'_{EAx}$>N'EAx_min, this means that the average cycle that would result would not be significant; it is then decided to extract no characteristic of the selected $EA_X$ components, the number of which is not sufficient.

Keeping only the j indices of the selected cycles, the following values are defined (with j≠reference_cycle_ind_EAx):

$$EAx\_correl\_coeff=average(r_{reference\_cycle\_ind\_EAx,j}),$$

and $$EAx\_correl\_delay=average(\tau_{reference\_cycle\_ind\_EAx,j})$$

The next step, corresponding to the block 16 of FIG. 3, is to generate an average cycle from the EA1 and EA2 components separately preprocessed as indicated above. To this end, the EA1 and EA2 sub-signals of each cycle are realigned compared to the reference sub-signal reference_cycle_ind_EAx. The first step involves centering the τreference_cycle_ind_Eax,j values, calculated in the previous step by subtracting the average value of the τreference_cycle_ind_EAx,j over all j (including the reference cycle). These new values of τreference_cycle_ind_EAx,j are then used to realign the EA1 and EA2 sub-signals relatively to the reference sub-signal reference_cycle_ind_EAx. Once the sub-signals are realigned, calculating an average EA1 or EA2 component and thus forming the average EA signal by using a combination of the two components is sufficient.

Figure 6:
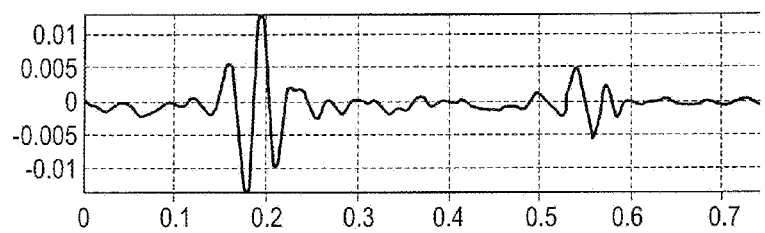
FIG. 6 illustrates the generation of an average cycle from the pre-processed data for each of the two EA1 and EA2 components of FIG. 4.

The average overall EA signal, defined over a period of one cycle is shown in FIG. 6.

Processing as described above, to generate an overall average cycle signal EA, is described in EP 2092885 A1 and its counterpart US Patent Publication No. 2009/0209875 cited above, which can be referred to for more details and which is incorporated herein by reference in its entirety.

As mentioned above, one embodiment of this processing involves a number of compromises between accuracy and speed of response, and these compromises can lead to a global average EA signal badly reflecting small variations in the hemodynamic status of the patient, or revealing significant sudden changes only with a delay that does not allow for efficiently exploiting the EA signal.

The present invention thus directed to improving this processing, allowing a dynamic adaptation of the various parameters and criteria for selection or elimination of insignificant cycles.

The modifiable parameters are preferably selected from among the following:

The number N of cycles of which the processing operates;
The step (step) between two processing sequences (with possibly overlapping in the successive sequences); and
The length of the analysis windows of the EA1 and EA2 components.

The modified validation criteria include:
The minimum threshold of the correlation coefficient with respect to the reference cycle,
The minimum of the temporal calibration relative to the reference cycle,
The minimum number N'EAx_min of cycles remaining after selection,
A flag indicating whether to reject a cycle as soon as one of the EA1 or EA2 sub-signals does not meet the validation criteria, or to accept the cycle only if the two EA1 and EA2 sub-signals both meet the validation criteria.

The adaptation of these parameters and validation criteria based on the current status of the patient allows optimizing the operation and responsiveness of the EA signal processing by benefiting from:

a reduction of the response time to obtain the average overall EA signal, when quick result is needed, and
the increase in the accuracy of the average overall EA signal obtained when the heart is not in a steady state condition, especially during periods of unstable heart rhythm.

Events or status changes that can be taken into account to change the settings or validation criteria of the processing may include:

A particular development of one of the factors of the EA signal (e.g., a drop in the peak-to-peak amplitude PEA1 of the EA1 component) or of an MV signal (e.g. hyperventilation), or again from a signal of patient activity (effort);
A suspicion or a detection of arrhythmia;
An apnea or hypopnea detection;
An imposed manual release (by the physician or by the patient); and
An acceleration of the cardiac rhythm.

The increase in accuracy can also be chosen in situations wherein there is no emergency, for example, during periods of sleep of the patient.

It may also be desirable to tailor the processing to reduce the computational load on the processor when not needed, thus preserving the autonomy and useful life of the battery of the device. Choosing a higher (larger) step allows in particular reducing the computational load, with as a consequence a less frequent update of the value of the average overall EA signal.

Regarding the validation criteria, if one chooses strict criteria (e.g., high correlation coefficient threshold, low temporal delay threshold, high minimum number of correct cycles), these changes lead to a larger rejection rate of cycles, with better final quality of the average overall EA signal, but with the risk, frequently, of getting no average overall EA signal, if the selected criteria are too strict.

With regard to the number N of cycles on which the averaging processing is performed, a large number N increases the time needed to get the average overall EA signal, but with a better quality of results, particularly in the case of a cyclostationary signal. Conversely, a decrease in the number N of cycles provides results much faster and is more suited to the case of a non-cyclostationary signal.

Finally, the durations of the analysis windows of the EA1 and EA2 components can be increased in case of a slow rhythm, and reduced in case of a rapid rhythm.

FIG. 7 illustrates the general principle of the dynamic adjustment of the processing according to the invention. For each new acquired and individualized EA signal cycle, as described above (block 20), this cycle is added to the stack of sampled values formed with the N previous cycles (block 22). The process then analyzes the type of response required (block 24). This question can be achieved by obtaining from the memory of the device the various indicators produced by the analysis of the rhythm of the patient (e.g., an indicator of the occurrence of arrhythmia), the patient's condition (e.g. indicator of awakening), etc.

If no timely response is required, the calculation of the average overall EA signal is done on the basis of "slow" parameters and validation criteria (block 26). Otherwise, the "fast" parameters and validation criteria are selected (block 28).

The average cycle is then generated from the parameters and validation criteria thus selected (block 30) to give an average overall EA signal with, as appropriate, a fast or slow response time, and a signal quality more or less high, this preprocessed signal being then subjected to an analysis (block 32).

FIG. 8 shows a preferred embodiment of the operation in accordance with the present invention. In this case, the choice criterion between slow and fast parameters is the transition from sinus rhythm to ventricular tachycardia (VT).

In case of a sinus rhythm, it is known that the EA signal is relatively stable and does not vary much from one cycle to another, a fast response time is not necessary and a more accurate average signal can be obtained. In this case a relatively high correlation (Tc) and number of cycles (N) can be chosen, for example, Tc=0.6, and N=16 (block 26).

However, upon detection of a VT, a rapid response of the average cycle should be available, and furthermore it is known that the cycle to cycle variability of the EA signal may be large. In this case the number of cycles used in deriving the average may be halved (for example) and the correlation coefficient reduced. Hence, N can be reduced, for example, to N=8 cycles and the threshold correlation coefficient can be reduced, Tc=0.4, for example. In this way, the device is able to quickly assess the ability of the patient to tolerate the VT and quickly apply, if necessary, an appropriate therapy.

One skilled in the art will appreciate that the present invention can be performed by other than the embodiment disclosed herein, which are provided for purposes of illustration and not limitation.

The invention claimed is:

1. A device for analysis of an endocardial acceleration (EA) signal, wherein the device has one or more parameters, the device comprising:
   means for continuously collecting the EA signal over a sequence of cardiac cycles;
   means for dividing the collected EA signal into a plurality of EA sub-signals, wherein each of the plurality of EA sub-signals corresponds to a single cardiac cycle of the sequence of cardiac cycles;
   means for isolating in each of the plurality of EA sub-signals at least one EAx component, wherein the at least one EAx component is associated with one of an S1 heart sound, an S2 heart sound, an S3 heart sound, or an S4 heart sound, and wherein the means for isolating the at least one EAx component is configured to isolate the EAx component over an analysis window having a predefined duration, wherein the analysis window comprises a timeframe during which isolation of the at least one EAx component is performed;
   means for cross-correlating the EAx components of the plurality of EA sub-signals, wherein the means for cross-correlating comprises:
   means for defining a reference cycle comprising a reference EA sub-signal;
   means for determining, for each of the plurality of EA sub-signals, a correlation coefficient based on the cross-correlation between the respective EA sub-signal and the reference EA sub-signal;
   means for determining, for each of the plurality of EA sub-signals, a calibration delay to calibrate the respective EA sub-signal against the reference EA sub-signal;
   means for determining a plurality of validation criteria;
   means for selecting a subset of EA sub-signals from among the plurality of EA sub-signals based on the plurality of validation criteria;
   means for averaging the selected subset of EA sub-signals and generating an output average overall EA sub-signal;
   means for detecting one of a change in a condition of a patient or an occurrence of a predetermined event in the patient; and
   means for dynamically adapting, on detection of said change of the condition or said predetermined event, at least one of said validation criteria or at least one of the one or more parameters of the device.

2. The device of claim 1, wherein the one or more parameters of the device comprise at least one of the following and the means for dynamically adapting further comprises means for modifying at least one of the following:
   a number of cardiac cycles within the sequence of cardiac cycles over which the EA signal is collected;
   a time interval between two successive collected and processed sequences; and
   the predefined duration of the analysis window over which the means for isolating the at least one EAx component is configured to isolate the EAx component.

3. The device of claim 1, wherein the validation criteria comprise at least one of the following and the means for dynamically adapting further comprises means for modifying at least one of the following:
   a minimum threshold correlation coefficient value for the correlation coefficient;
   a maximum threshold calibration delay value for said calibration delay to calibrate the respective EA sub-signal against the reference EA sub-signal;
   a minimum number of EA sub-signals selected from among the plurality of EA sub-signals based on the plurality of validation criteria by the means for selecting; and
   if each EA sub-signal includes a plurality of EAx components, a validation requirement that the means for selecting select a particular EA sub-signal for inclusion within the subset of EA sub-signals only when all EAx components of the particular EA sub-signal satisfy the validation criteria.

4. The device of claim 1, wherein said change of the condition of the patient or predetermined event is selected from among the group consisting of: an increased heart rate, a heart rate instability, a decreased amplitude of a peak of endocardial acceleration, an increase in a ventilation rhythm, an apnea detection, and an application of an external command.

* * * * *